United States Patent
Chmielewski et al.

(10) Patent No.: US 8,884,005 B2
(45) Date of Patent: Nov. 11, 2014

(54) METHOD FOR THE PREPARATION OF CARBAPENAM COMPOUNDS

(75) Inventors: Marek Chmielewski, Warsaw (PL); Bartlomiej Furman, Wólka Radzymińska (PL); Sebastian Stecko, Zabrze (PL); Irma Panfil, Warsaw (PL); Margarita Jurczak, Warsaw (PL); Paulina Mikolajczyk, Warsaw (PL); Magdalena Soluch, Tomaszów Lubelski (PL)

(73) Assignee: Instytut Chemi Organicznej Pan, Warsaw (PL)

( * ) Notice: Subject to any disclaimer, the term of this patent is extended or adjusted under 35 U.S.C. 154(b) by 0 days.

(21) Appl. No.: 13/985,478

(22) PCT Filed: Feb. 14, 2012

(86) PCT No.: PCT/PL2012/050005
§ 371 (c)(1),
(2), (4) Date: Jan. 27, 2014

(87) PCT Pub. No.: WO2012/112061
PCT Pub. Date: Aug. 23, 2012

(65) Prior Publication Data
US 2014/0148595 A1    May 29, 2014

(30) Foreign Application Priority Data
Feb. 14, 2011    (PL) .......................... 393916

(51) Int. Cl.
C07D 487/04    (2006.01)
C07D 477/04    (2006.01)
C07D 477/26    (2006.01)
C07D 519/06    (2006.01)
C07D 477/00    (2006.01)

(52) U.S. Cl.
CPC ............ C07D 477/04 (2013.01); C07D 477/26 (2013.01); C07D 519/06 (2013.01); C07D 477/00 (2013.01)
USPC .......................................................... 540/302

(58) Field of Classification Search
CPC ...................................................... C07D 519/06
See application file for complete search history.

(56) References Cited

FOREIGN PATENT DOCUMENTS

WO    WO 2012112061 A1 *   8/2012

OTHER PUBLICATIONS

Khangarot et al., "A stereoselective synthesis of sugar-derived chiral [beta]-lactams," European Journal of Oranic Chemistry (Aug. 18, 2011), 2011(30):6117-6127.

* cited by examiner

*Primary Examiner* — Noble Jarrell
*Assistant Examiner* — John S Kenyon
(74) *Attorney, Agent, or Firm* — Fox Rothschild LLP; Shahnam Sharareh

(57) ABSTRACT

The subject of the present invention is a method of the preparation of compounds containing the core skeleton of carbapenem antibiotics, novel intermediate compounds used in this method, a method of the preparation of the intermediate compounds as well as the use of the intermediate compounds in the production of carbapenem antibiotics.

19 Claims, No Drawings

METHOD FOR THE PREPARATION OF CARBAPENAM COMPOUNDS

This application is a U.S. National Phase Application based on International Application PCT/PL2012/050005 filed Feb. 14, 2012, which claims priority to Poland Application No. P. 393916 filed Feb. 14, 2011. The disclosures of both applications are incorporated herein by reference in their entirety.

The present invention relates to a method of the preparation of compounds containing the core skeleton of carbapenem antibiotics, novel intermediate compounds used in this method, a method of the preparation of the intermediate compounds as well as the use of the intermediate compounds in the production of carbapenemate antibiotics.

Thienamycin (1) is the best known, natural carbapenem antibiotic with a high pharmacological activity. Derivatives of thienamycin such as Imipenem (2), Panipenem (3), Doripenem (4), Meropenem (5), Ertapenem (6), Biapenem (7), Razupenem (8) are the active ingredients of known pharmaceutical therapeutics with anti-inflammatory activity, and high resistance to β-lactamases, bacterial enzymes that destroy administered antibiotics.

FIG. 1

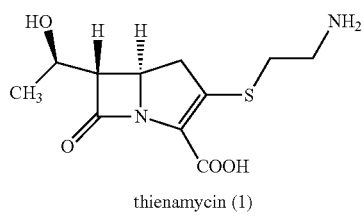

thienamycin (1)

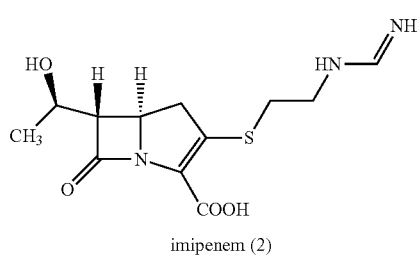

imipenem (2)

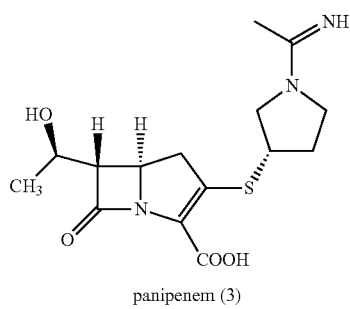

panipenem (3)

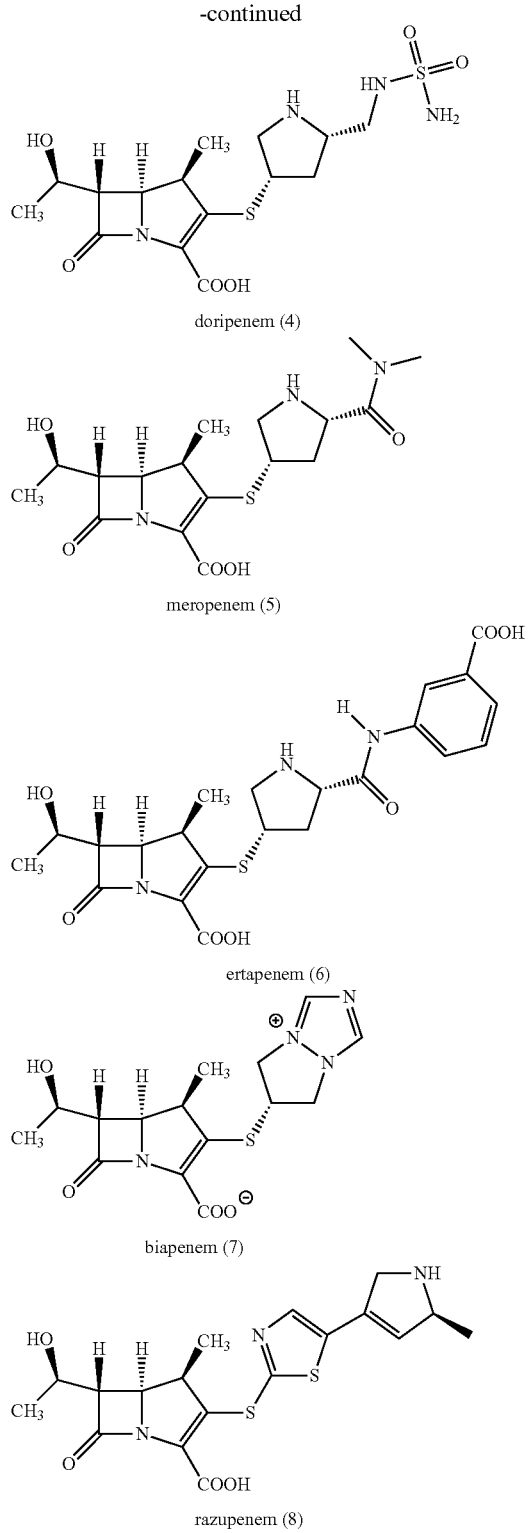

doripenem (4)

meropenem (5)

ertapenem (6)

biapenem (7)

razupenem (8)

The invention relates to a method of the preparation of the core skeleton of carbapenam antibiotics defined by the general formula 9, intermediate compounds, a method of the preparation of intermediate compounds, as well as the use of the intermediate compounds, based on the reaction of terminal acetylene compounds defined by the general formula 10 with cyclic five-membered nitrones defined by the general formula 11 in the presence of copper(I) salts, called the Kinugasa reaction, according to Scheme 1.

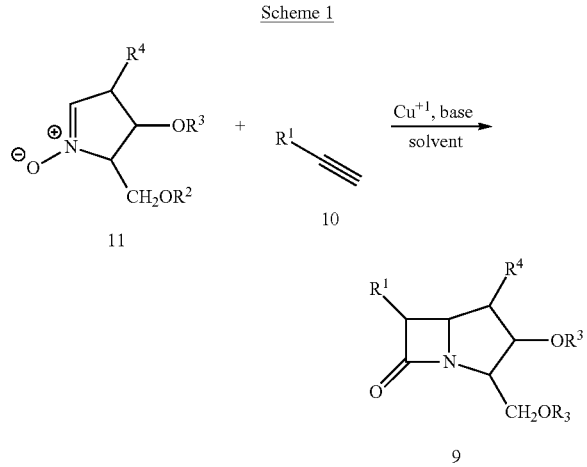

Scheme 1

The received β-lactam compounds 9 may then be subjected to numerous transformations that make them possible to obtain selected active ingredients of drugs with a high pharmacological activity. In particular, group $R^1$ may be transformed into an alkyl or hydroxyalkyl substituent (with a free or protected hydroxyl group), the $CH_2OR^2$ group may be oxidized to a carboxyl group, the substituent $OR^3$ makes it possible to introduce the side chains occurred in carbapenem antibiotics, and group $R^4$ remains unchanged, or may be exchanged for another substituent.

The subject of the present invention is a method of the preparation of a β-lactam compound defined by the general formula 9 in which:
- $R^1$ denotes a linear or branched substituent: a $C_{1-6}$-alkyl, $C_{3-6}$-alkene, a hydroxy-$C_{1-6}$-alkyl, an O-protected hydroxy-$C_{1-6}$-alkyl, a dihydroxy-$C_{1-6}$-alkyl or an O,O'-protected dihydroxy-$C_{1-6}$-alkyl (wherein both hydroxyl groups may have the same or different protecting groups, in particular the protection of both hydroxyl groups may be a cyclic acetal or ketal group),
- $R^2$ denotes a linear or branched $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl or acyl group;
- $R^3$ denotes an $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl or acyl group;
- $R^2$ and $R^3$ may denote a cyclic acetal or ketal group;
- $R^4$ denotes a hydrogen atom, or methyl, $C_{1-6}$-alkoxyl, $C_{1-6}$-alkoxymethyl, allyl benzyloxymethyl, benzyloxyl, siloxyl or acyloxyl group.

According to the present invention, substrates in the synthesis of a β-lactam compounds defined by the general formula 9 are acetylene compounds defined by the general formula 10 and nitrones defined by the general formula 11.

The acetylene compound 10 is characterised in that:
- $R^1$ denotes a linear or branched $C_{1-6}$-alkyl, $C_{3-6}$-alkene, $C_{1-6}$-alkoxymethyl, benzyloxymethyl, hydroxy-$C_{1-6}$-alkyl, O-protected hydroxy-$C_{1-6}$-alkyl, dihydroxy-$C_{1-6}$-alkyl (also O,O'-protected dihydroxy-$C_{1-6}$-alkyl) group, in particular a 1,1-dihydroxy-$C_{1-6}$-alkyl, 1,2-dihydroxy-$C_{1-6}$-alkyl as well as a 1,3-dihydroxy-$C_{1-6}$-alkyl group, as is shown below:

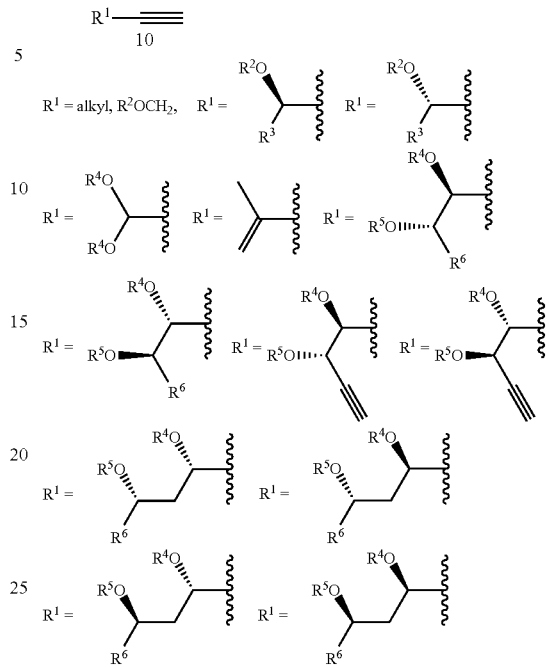

FIG. 2 where:
- $R^2$ denotes a linear or branched $C_{1-6}$-alkyl, allyl, benzyl (including a benzyl group substituted in the benzene ring), $C_{1-6}$-alkoxymethyl, benzyloxymethyl, silyl, or acyl group;
- $R^3$ denotes linear or branched $C_{1-6}$-alkyl or aryl group;
- $R^4$ denotes a linear or branched $C_{1-6}$-alkyl, allyl, benzyl (including a benzyl group substituted in the benzene ring), $C_{1-6}$-alkoxymethyl, benzyloxymethyl, silyl, or acyl group;
- $R^5$ denotes a linear or branched $C_{1-6}$-alkyl, allyl, benzyl (including a benzyl group substituted in the benzene ring), $C_{1-6}$-alkoxymethyl, benzyloxymethyl, silyl, or acyl group;
- $R^4$ and $R^5$ may denote a cyclic acetal or ketal group, or carbonate forming a fragment of the 1,3-dioxolane, 1,3-dioxane, or 1,4-dioxane ring;
- $R^6$ denotes a hydrogen atom, linear or branched $C_{1-6}$-alkyl or aryl group.

A method of preparation acetylene compounds defined by the formula 10 is known (J. Pietruszka, A. Witt, *J. Chem. Soc., Perkin Trans.* 1, 2000, 4293-4300) and is based on the reaction of the corresponding aldehyde defined by the general formula $R^1$—CHO, in which:
- $R^1$ denotes a linear or branched $C_{1-6}$-alkyl, $C_{3-6}$-alkene, $C_{1-6}$-alkoxymethyl, benzyloxymethyl, hydroxy-$C_{1-6}$-alkyl, O-protected hydroxy-$C_{1-6}$-alkyl, dihydroxy-$C_{1-6}$-alkyl (also O,O'-protected dihydroxy-$C_{1-6}$-alkyl) group, in particular 1,1-dihydroxy-$C_{1-6}$-alkyl, 1,2-dihydroxy-$C_{1-6}$-alkyl as well as 1,3-dihydroxy-$C_{1-6}$-alkyl as shown in FIG. 1, where:
- $R^2$ denotes a linear or branched $C_{1-6}$-alkyl, allyl, benzyl (including a benzyl group substituted in the benzene ring), $C_{1-6}$-alkoxymethyl, benzyloxymethyl, silyl, or acyl group;
- $R^3$ denotes linear or branched $C_{1-6}$-alkyl or aryl group;
- $R^4$ denotes a linear or branched $C_{1-6}$-alkyl, allyl, benzyl (including a benzyl group substituted in the benzene ring), $C_{1-6}$-alkoxymethyl, benzyloxymethyl, silyl, or acyl group;

R[5] denotes a linear or branched $C_{1-6}$-alkyl, allyl, benzyl (including a benzyl group substituted in the benzene ring), $C_{1-6}$-alkoxymethyl, benzyloxymethyl, silyl, or acyl group;

R[4] and R[5] may denote a cyclic acetal or ketal group, or carbonate forming a fragment of the 1,3-dioxolane, 1,3-dioxane, or 1,4-dioxane ring;

R[6] denotes a hydrogen atom, linear or branched $C_{1-6}$-alkyl or aryl group.

with the Bestmann-Ohira reagent $CH_3C(=O)C(=N_2)P(=O)(OMe)_2$, according to Scheme 2. The Bestmann-Ohira reagent is prepared using a known method (J. Pietruszka, A. Witt, *Synthesis* 2006, 24, 4266-4268).

Scheme 2

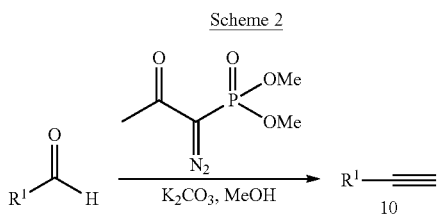

The reaction can occur at a wide range of temperatures and the precise temperature has no particular significance for the reaction. A preferable reaction temperature depends on such factors as the type of solvent, source materials used or reagents. However, it is usually preferable to conduct the reaction at a temperature between −60° C. and 60° C., more preferably between −40° C. and 20° C.

The reaction time may also vary over a wide range, depending on many factors, especially the reaction temperature and type of source materials used, as well as the solvent. However, the reaction time usually is from 1 hour to 72 hours, more preferably from 6 hours to 48 hours.

It is particularly preferable when acetylene compound 10 is produced from L-lactic acid or D-lactic acid or L-glyceraldehyde or D-glyceraldehyde or L-malic acid or D-malic acid or L-tartaric acid or D-tartaric acid.

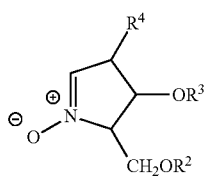

Cyclic nitrones defined by the general formula 11, where:

R[2] denotes a linear or branched $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl or acyl group;

R[3] denotes an $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl or acyl group;

R[2] and R[3] may denote a cyclic acetal or ketal group;

R[4] denotes a hydrogen atom, or methyl, $C_{1-6}$-alkoxyl, $C_{1-6}$-alkoxymethyl, allyl benzyloxymethyl, benzyloxyl, siloxyl or acyloxyl group is characterised in that it is produced using a known method from the readily available sugars: D- or L-arabinose, D- or L-xylose, D- or L-ribose, or 2-deoxy-D-ribose.

A method of producing nitrones defined by the formula 11 is known (P. Vogel et al. *Helv. Chim. Acta* 2003, 86, 3066-3073; S. Py et al. *J. Org. Chem.* 2005, 70, 1459-462; C.-Y. Yu et al. *Synlett* 2010, 488-492) and is based on the production of an appropriate alkyl pentofuranoside from a commercially available pentose, in which the primary hydroxyl group is then blocked, or transformed into alkoxycarbonyl function, and then the secondary group or groups or all hydroxyl groups are blocked in one, or two reaction stages. The resulting glycoside is hydrolysed, which results in the formation of a 2,3,5-trisubstituted, or 3,5-disubstituted pentafuranose. Treatment of the 2,3,5-trisubstituted or 3,5-disubstituted pentofuranose with an O-tert-butyldiphenylsilylhydroxylamine provides corresponding oxime, in which then the free hydroxyl group is activated through transformation into an appropriate mesylate or exchanged into halogen. Desilylation of the oxime followed by subsequent N-alkylation leads to the formation of nitrones defined by the general formula 11.

According to the present invention, β-lactam compound defined by general formula 9 is produced. β-Lactam compound defined by the formula 9, is an important intermediate product in the production of carbapenem antibiotics using readily available, inexpensive starting materials and reagents.

According to the present invention, a reaction of the nitrone compound defined by the formula 11, with an acetylene compound defined by the formula 10 in the presence of a base and a copper(I) salt, possibly in the solvent, highly stereoselectively produces a compound defined by the formula 9, containing a four-membered β-lactam ring condensed with a five-membered pyrrolidine ring (Scheme 1).

In one embodiment, the copper salt includes at least one from a group comprising copper(I) iodide, copper(I) bromide, copper(I) chloride copper(I) acetate and copper(I) triflate.

In other embodiment, as the copper source at least one copper(II) compound is used with an addition of a reducing compound, preferably selected from a group encompassing the combinations: copper(II) sulphate/sodium ascorbate, copper(II) chloride/sodium ascorbate and copper(II) acetate/sodium ascorbate.

Particularly, at the most 3 equivalents of the copper compound, relative to compound 10, are used, and preferably from 0.01 to 1 equivalent of the copper compound, relative to compound 10, are used.

Preferably, for the reaction of the compound defined by the formula 10 with the compound defined by the formula 11 secondary or tertiary amine is used as a base.

In particular, an amine is selected from group comprising trialkylamines, such as triethylamine or N,N-diisopropylethylamine, alkyldi(cycloalkyl)-amines, such as N-methyldicyclohexylamine, tetramethylguanidine, dialkylamines possessing branched substituent alkyls, such as diisopropylamine, di(cycloalkyl)amines, such as dicyclohexylamine, as well as heterocyclic amines, such as pyridine. The preferred amine is triethylamine.

Preferably, triethylamine in an amount of at least 3 equivalents relative to copper source is used.

Preferably, for the reaction of the compound defined by the formula 10 with the compound defined by the formula 11 alkali metal or alkaline earth metal carbonates are used as a base.

In particular, a base selected from a group encompassing potassium carbonate, sodium carbonate, sodium bicarbonate, potassium bicarbonate is used.

For the reaction of the compound defined by the formula 10 with the compound defined by the formula 11 the solvent is selected from a group encompassing aromatic hydrocarbons, chlorinated aliphatic hydrocarbons, aliphatic ethers, aliphatic nitriles, aliphatic N,N-di-($C_{1-6}$-alkyl)amides.

Preferably, the solvent selected from a group encompassing acetonitrile, toluene, benzene, N,N-dimethylformamide, N,N-dimethylacetamide, tetramethylguanidine, HMPA, N-methylpyrrolidone is used.

The reaction of the nitrone compound defined by the formula 11, with an acetylene compound defined by the formula 10 in the presence of a base and a copper(I) compound, possibly in the solvent, produces with high stereoselectivity a compound defined by the formula 9, containing a four-membered β-lactam ring fused to the five-membered pyrrolidine ring, in which the protected hydroxymethyl group $CH_2OR^2$ may be easily transformed into a carboxyl group, and group $R^1$ possesses a substituent alkyl or hydroxyalkyl, whereas protected hydroxyl group $R^3$ makes it possible to connect the side chain of the antibiotics.

Scheme 3

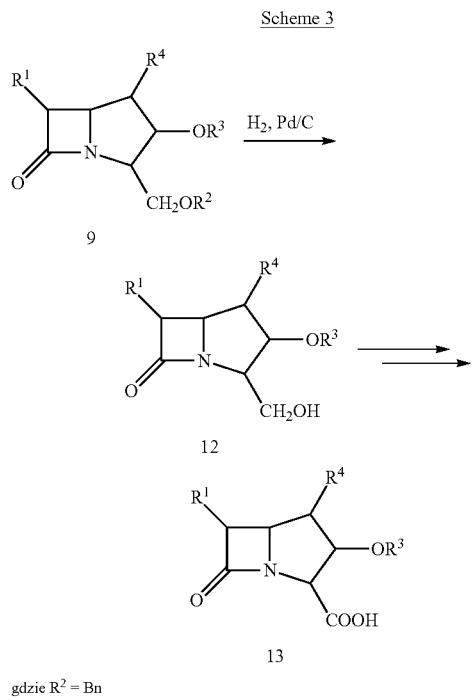

gdzie $R^2$ = Bn

For example, when in the compound 9 produced, according to the present invention, in the reaction of the nitrone compound defined by the formula 11, with an acetylene compound defined by the formula 10 in the presence of a base and copper(I) compound, possibly in the solvent, substituent $R^2$ denotes a benzyl group, this group may be selectively removed, resulting in compound 12, in which the $CH_2OH$ group may be oxidized to a carboxyl group (13) using known methods (Tojo, G, Fernandez, M. *Oxidation of Primary Alcohols to Carboxylic Acids. A Guide to Current Common Practice.* Springer: N.Y. 2007; Furman, B.; Molotov, S.; Türmer, R.; Kałuża, Z.; Voelter, W.; Chmielewski, M. *Tetrahedron* 1997, 53, 5883-5890) (Scheme 3). The carboxyl group is a key structural element of known carbapenemate compounds (FIG. 1).

The subject of the present invention has been illustrated in the example embodiments.

EXAMPLES

Example 1

Synthesis of Carbapenam 14 from Nitrone 15, derived from 2-Deoxyribose, and Diethoxypropyne

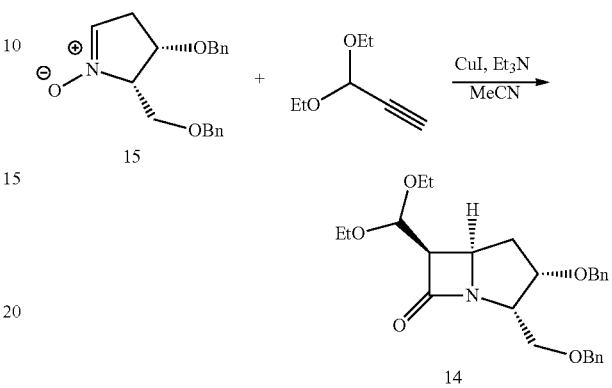

Triethylamine (0.56 ml, 4.0 mmol) was added to a suspension of copper(I) iodide (1.0 mmol, 190 mg) in acetonitrile (5 ml) under an inert gas atmosphere. After cooling to 0° C., diethoxypropyne (1.0 mmol, 128 mg, 145 µl) was added. The resulting solution was stirred at 0° C. for 20 min. and then a solution of the nitrone 15, derived from 2-deoxy-D-ribose, (1.0 mmol, 311 mg) in acetonitrile (5 ml) was added. The resulting mixture was stirred under an inert gas atmosphere for 24 hours. Subsequently, the mixture was diluted with diethyl ether (20 ml), filtered through Celite and concentrated under diminished pressure. The residue was chromatographed on a neutralised silica gel using a hexane/ethyl acetate mixture (2:1) as the eluent to afford compound 14 (263 mg, 60%) as a white solid.

$[α]_D$+10.4 (c 1, $CH_2Cl_2$); $^1$H NMR (600 MHz, $C_6D_6$), δ: 7.30-6.98 (10H, 2×Ph), 4.53 (1H, d, J 6.2 Hz, H-1'), 4.33 (1H, d, J 12.0 Hz, OCHHPh), 4.28 (1H, d, J 12.0 Hz, OCHHPh), 4.12-4.07 (2H, m, H-6, H-7), 3.73 (1H, m, H-4), 3.64 (1H, d, J 9.5, 6.3 Hz, H-8a), 3.60 (1H, d, J 9.5, 5.4 Hz, H-8b), 3.50-3.31 (5H, H-3, 2×$OCH_2CH_3$), 1.98 (1H, ddd, J 13.5, 6.7, 3.6 Hz, H-5a), 1.87 (1H, ddd, J 13.5, 7.5, 5.5 Hz, H-5b), 1.05 (3H, t, J 7.1 Hz, $OCH_2CH_3$), 0.99 (3H, t, J 7.1 Hz, $OCH_2CH_3$); $^{13}$C NMR (150 MHz, $C_6D_6$, carbon atoms of the Ph group are omitted) δ: 175.5, 99.3, 82.9, 72.9, 71.9, 68.3, 62.4, 61.7, 60.8, 54.9, 53.5, 32.3, 15.09, 15.07; IR (film) 1764 $cm^{-1}$; HRMS (ESI) m/z calcd for $C_{26}H_{33}NO_5Na$ [M+Na$^+$] 462.2251; Found: 462.2271.

Example 2

The Synthesis of Carbapenamate 16 from L-Arabino-Nitrone 17 and Diethoxypropyne

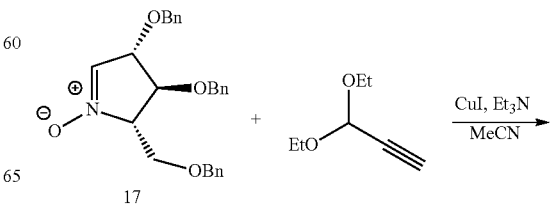

-continued

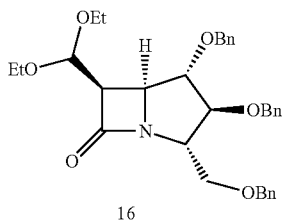

16

The synthesis of carbapenam 16 was conducted as in Example 1. Yield: 56%.

[α]$_D$+27.6 (c 2.0, CHCl$_3$); $^1$H NMR (600 MHz, C$_6$D$_6$) δ: 7.30-7.00 (15H, 3×Ph), 4.83 (1H, d, J 8.1 Hz, H-1'), 4.52 (1H, m), 4.42-4.33 (5H, m), 4.30-4.22 (3H, m), 3.75 (1H, dd, J 8.2, 6.1 Hz), 3.66 (1H, dd, J 6.1, 2.7 Hz), 3.47 (1H, m), 3.51-3.45 (2H, m) 3.43-3.38 (2H, m), 3.20 (1H, m), 1.07 (3H, t, J 7.1 Hz), 0.92 (3H, t, J 7.1 Hz). IR (film) v: 1771 cm$^{-1}$; HRMS (ESI): m/z calcd for C$_{33}$H$_{39}$NO$_6$Na [M+Na$^+$] 568.2670; Found: 568.2673.

Example 3

The Synthesis of Carbapenam 18 from D-Xylo-Nitrone 19 and Diethoxypropyne

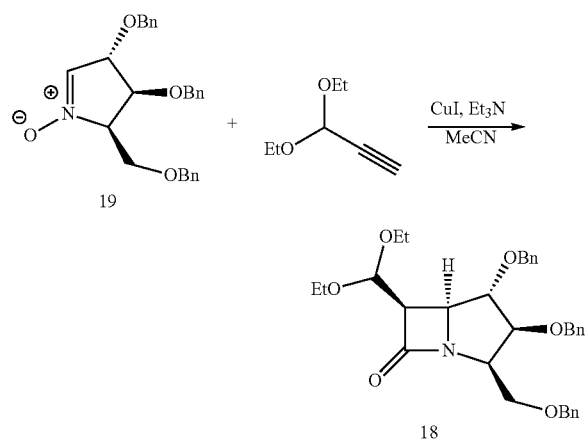

18

The synthesis of carbapenam 18 was conducted as in Example 1.

[α]$_D$−5.3 (c 1, CH$_2$Cl$_2$); $^1$H NMR (600 MHz, C$_6$D$_6$) δ: 7.27-7.04 (15H, 3×Ph), 4.88 (1H, d, J 9.1 Hz, H-1'), 4.45 (1H, dd, J 9.8, 7.7 Hz, H-8a), 4.42-4.33 (7H, H-8b, 2×OCH$_2$CH$_3$, OCH$_2$Ph), 4.19 (1H, dd, J 9.4, 4,2 Hz, H-7), 4.12 (1H, dd, J 3.8, 2.1 Hz, H-5), 3.70 (1H, m, H-6), 3.67 (1H, dd, J 9.1, 6.1 Hz, H-3), 3.57 (1H, dd, J 6.1, 2.1 Hz, H-4), 3.53 (1H, m, OCHHPh), 3.43 (1H, m, OCHHPh), 3.36 (1H, m, OCHHPh), 3.21 (1H, m, OCHHPh), 1.12 (3H, t, J 7.1 Hz, OCH$_2$CH$_3$), 0.96 (3H, t, J 7.0 Hz, OCH$_2$CH$_3$). $^{13}$C NMR (150 MHz, C$_6$D$_6$, carbon atoms of the Ph group are omitted) δ: 174.5, 99.5, 86.1, 80.7, 73.5, 72.3, 71.8, 64.9, 64.2, 63.4, 59.9, 59.1, 56.1, 15.6, 15.4; IR (film) 1770 cm$^{-1}$; HRMS (ESI): m/z calcd for C$_{33}$H$_{39}$NO$_6$Na [M+Na$^+$] 568.2670; Found: 568.2661.

Example 4

The Synthesis of Carbapenams 20a,b from Nitrone 15 and 1-(t-butyldiphenylsiloxy)-prop-2-yne 21

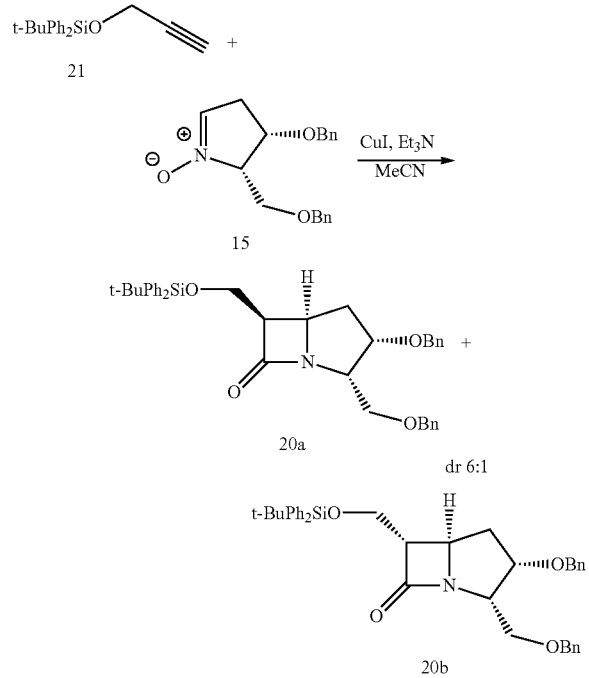

The synthesis of carbapenams 20a,b was conducted as in Example 1. Overall yield: 64%. Main product 20a: [α]$_D$+6.6 (c 1, CH$_2$Cl$_2$); $^1$H NMR (500 MHz, CDCl$_3$) δ: 7.67-7.20 (20H, 4×Ph), 4.60-4.50 (m, 3H), 4.44 (1H, d, J 11.8 Hz), 4.32 (m, 1H), 4.03-3.98 (m, 2H), 3.95 (1H, dd, J 11.3, 4.5 Hz), 3.79 (1H, dd, J 0.3, 9.4 Hz), 3.68-3.58 (m, 3H), 2.09 (1H, ddd, J 13.4, 6.6, 4.0 Hz), 1.90 (1H, ddd, J 13.6, 7.4, 5.7 Hz), 1.05 (s, 9H); $^{13}$C NMR (125 MHz, CDCl$_3$, the signals of the carbons from the Ph group are omitted) δ: 177.6, 83.5, 73.3, 72.4, 67.9, 60.6, 59.1, 54.5, 53.1, 31.5, 26.8, 19.1; IR (film) v: 1763, 1112 cm$^{-1}$; HR MS (ESI) m/z calcd for C$_{38}$H$_{43}$NO$_4$SiNa [M+Na$^+$] 628.2854. Found: 628.2878.

Example 5

The Synthesis of Carbapenams 22a,b from Nitrone 15 and 1-(t-butyldiphenylsiloxy)-prop-2-yne 23

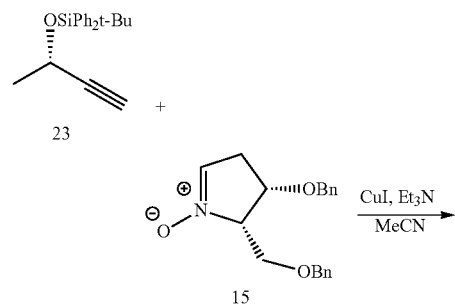

-continued

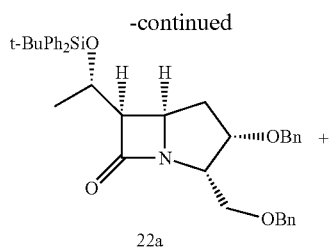

22a dr 6:1

22b

The synthesis of carbapenams 22a,b was conducted as in Example 1. Overall yield: 64%. main product 22a: [α]$_D$+1.7 (c 1, CH$_2$Cl$_2$); $^1$H NMR (500 MHz, CDCl3) δ: 7.73-7.21 (20H, 4×Ph), 4.57-4.49 (m, 2H), 4.38 (1H, d, J 11.8 Hz), 4.32 (1H, d, J 11.8 Hz), 4.13 (1H, m), 4.00-3.91 (2H, m), 3.86 (1H, m), 3.63 (1H, dd, J 9.6, 6.6 Hz), 3.56 (1H, dd, J 96, 6.4 Hz), 3.47 (1H, dd, J 9.6, 5.4 Hz), 1.87 (1H, ddd, J 13.4, 6.1, 3.4 Hz), 1.49 (1H, ddd, J 13.6, 8.1, 5.4 Hz), 1.26 (3H, d, J 6.1 Hz); 1.02 (9H, s); 13C NMR (125 MHz, CDCl3, the carbon atoms of the Ph group were omitted) δ: 177.7, 83.4, 73.2, 72.1, 67.9, 66.3, 60.7, 58.4, 55.1, 32.3, 26.9, 22.6, 19.1. IR (film) v: 1760 cm$^{-1}$; HR MS (ESI) m/z calcd for C$_{38}$H$_{43}$NO$_4$SiNa [M+Na$^+$] 628.2854; Found: 628.2880.

Example 6

The Selective Monodebenzylation of Carbapenam 14. The Synthesis of Carbapenam 24

To a solution of carbapenam 14 (100 mg, 0.22 mmol) in methanol (8 ml) 10% Pd/C (10 mg) was added and the resulting suspension saturated with hydrogen at room temperature for 12 h. After filtering through Celite and removal the solvent, the residue was chromatographed on silica gel (hexane/ ethyl acetate 7:3) yielding 17 mg (23%) of carbapenam 24 as a clear oil.

[α]$_D$+19.2 (c 1, CH$_2$Cl$_2$); $^1$H NMR (500 MHz, CDCl$_3$) δ: 7.37-7.22 (5H, Ph), 4.70 (1H, d, J 5.5 Hz), 4.61 (1H, d, J 12.0 Hz), 4.50-4.44 (2H, m), 4.02-3.93 (2H, m), 3.80-3.50 (7H, m), 2.25-2.13 (3H, m), 1.20 (3H, t, J 7.0 Hz), 1.15 (3H, t, J 7.0 Hz); $^{13}$C NMR (125 MHz, CDCl$_3$, carbon atoms of the Ph group are omitted), δ: 176.3, 99.1, 83.9, 72.4, 62.9, 62.3, 61.9, 61.4, 55.3, 53.5, 31.9, 15.24, 15.22; IR (film) v: 3422, 1763, 1624, 111, 1057 cm$^{-1}$; HRMS (ESI): m/z calcd for C$_{19}$H$_{27}$NO$_5$Na [M+Na$^+$] 372.1781; Found: 372.1774.

Example 7

The Synthesis of Bis(Carbapenam) 25 from Nitrone 15, derived from 2-Deoxyribose and Bis(Acetylene) 26 derived from D-Tartaric Acid Bis(carbapenam) 25 was obtained as in Example 1. Yield: 67% [α]$_D$+19.2 (c 1, CH$_2$Cl$_2$); $^1$H NMR (600 MHz, CDCl$_3$) δ: 7.34-7.23 (20H, 4×Ph), 4.59-4.46 (m, 8H), 4.44 (m, 2H), 4.25 (m, 2H), 4.07 (m, 2H), 4.02 (m, 2H), 3.70 (m, 2H), 3.65 (dd, J 9.7, 6.2 Hz, 2H), 3.61 (dd, J 9.7, 6.1 Hz, 2H), 2.24-2.12 (m, 4H), 1.35 (s, 6H); $^{13}$C NMR (150 MHz, CDCl$_3$) δ: 176.2, 138.3, 138.0 128.4, 128.3, 127.7, 127.6, 127.5, 127.5, 109.8, 83.3, 75.0, 73.2, 72.3, 67.9, 60.9, 54.3, 52.7, 32.0, 26.9; IR (film) 1771 cm$^{-1}$.

Example 8

The Synthesis of Carbapenams 26 and 27 from Nitrone 15, derived from 2-Deoxyribose, and Acetylene 28

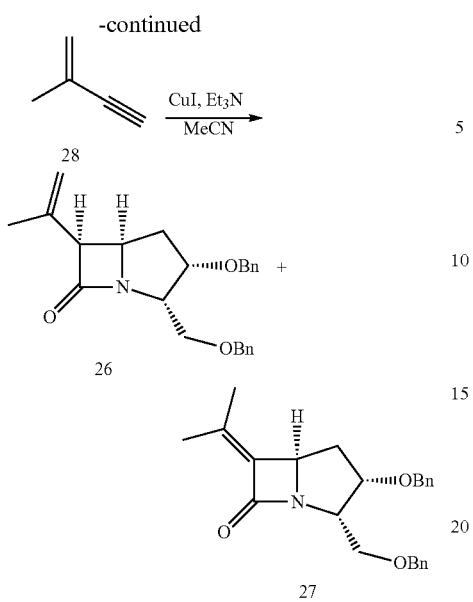

Triethylamine (4 mmol, 405 mg, 0.56 ml) was added to a suspension of CuI (2 mmol, 380 mg) in 5 ml MeCN. After cooling to 0° C. acetylene 28 (3 mmol, 200 mg) was added and after stirring for 10 min, solution of nitrone 15 (1 mmol, 315 mg) in 5 ml MeCN. After 8 h an additional portion of acetylene (2 mmol, 130 mg) was added. After 24 h the reaction mixture was diluted with ethyl acetate, filtered through Celite and concentrated under diminished pressure. The residue was chromatographed on silica gel (hexane/AcOEt 2:1) to afford 41 mg (11%) of carbapenam 26 and 200 mg (53%) of carbapenam 27. Carbapenam 26 $^1$H NMR (600 MHz, CDCl$_3$) δ: 7.40-7.20 (m, 10H), 5.09 (s, 1H), 4.97 (s, 1H), 4.59-4.47 (m, 4H), 4.31 (m, 1H), 4.06 (dt, J 8.0, 5.7 Hz, 1H), 4.01-3.99 (m, 2H), 3.68 (dd, J 9.6, 6.7 Hz, 1H), 3.63 (dd, J 9.6, 6.2 Hz, 1H), 2.12 (ddd, J 13.3, 5.8, 2.8 Hz, 1H), 1.66 (s, 3H), 1.55 (ddd, J 13.3, 8.0, 5.4 Hz, 1H); $^{13}$C NMR (150 MHz, CDCl$_3$) δ: 177.9, 138.2, 137.9, 136.9, 128.4, 128.3, 127.7, 127.69, 127.5, 127.4, 114., 83.5, 73.2, 72.3, 67.9, 61.1, 56.4, 55.4, 32.2, 22.1; IR (film) v: 1761, 1093 cm$^{-1}$; HR MS (ESI) m/z calcd for C$_{24}$H$_{27}$NO$_3$Na [M+Na$^+$] 400.1883. Found: 400.1891; Carbapenam 27; $^1$H NMR (600 MHz, CDCl$_3$) δ: 7.40-7.20 (m, 10H), 4.62-4.51 (m, 4H), 4.33-4.09 (m, 2H), 4.07-4.03 (q, J 5.6 H, 1H), 3.72 (dd, J 9.6, 6.0 Hz, 1H), 3.68 (dd, J 9.6, 5.6 Hz, 1H), 2.26 (ddd, J 13.1, 6.8, 5.2 Hz, 1H), 2.02 (s, 3H), 1.77 (dt, J 13.1, 6.0 Hz, 1H), 1.73 (s, 3H); $^{13}$C NMR (150 MHz, CDCl$_3$) δ: 173.8, 139.3, 138.4, 138.0 136.0, 128.5, 128.4, 128.3, 127.7, 127.6, 127.4, 83.4, 73.3, 72.4, 68.3, 60.5, 58.7, 34.8, 20.7, 20.2; IR (film) v: 1745, 1096 cm$^{-1}$; HR MS (ESI) m/z calcd for C$_{24}$H$_{27}$NO$_3$Na [M+Na$^+$] 400.1883. Found: 400.1892.

$R^2$ and $R^3$ taken together form a cyclic acetal or ketal group; and
$R^4$ is a compound selected from the group consisting of a hydrogen atom, methyl, $C_{1-6}$-alkoxyl, $C_{1-6}$-alkoxymethyl, allyl, benzyloxymethyl, benzyloxyl, siloxyl and acyloxyl group.
19. The compound of claim 18, wherein $R^1$ is selected from the group consisting of:
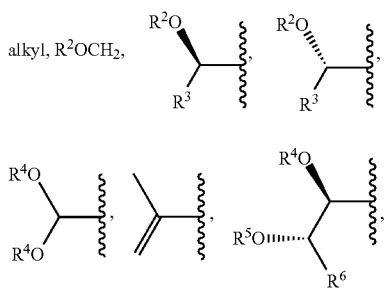
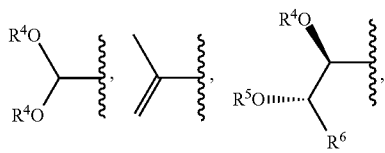
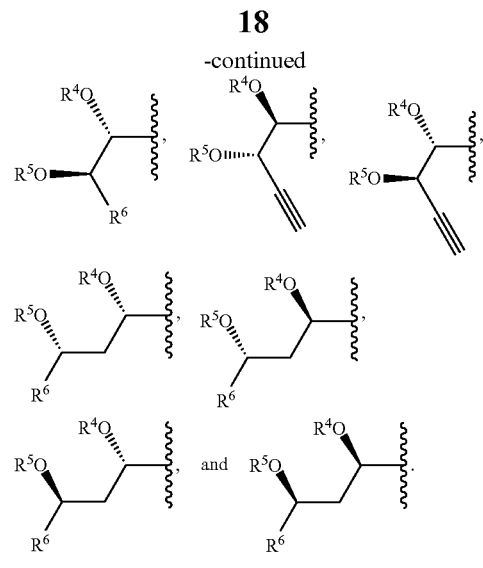

The invention claimed is:

1. A method of preparing a β-lactam compound defined by the formula 9,

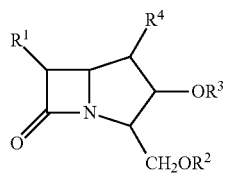

where:
R$^1$ is a C$_{1-6}$ alkyl, C$_{3-6}$-alkene, C$_{1-6}$-alkoxymethyl, benzyloxymethyl, a hydroxy-C$_{1-6}$-alkyl, an O-protected hydroxy-C$_{1-6}$-alkyl, a dihydroxy-C$_{1-6}$-alkyl or an O, O'-protected dihydroxy-C$_{1-6}$-alkyl wherein both hydroxyl groups may have the same or different protecting groups, and further wherein the protection of both hydroxyl groups is by a cyclic acetal or ketal group,
R$^2$ is a C-alkyl, allyl, benzyl, substituted benzyl, silyl, C$_{1-6}$-alkoxymethyl, benzyloxymethyl, C$_{1-6}$-alkylsulphonyl, arylsulphonyl or acyl group;
R$^3$ is a C$_{1-6}$-alkyl, allyl, benzyl, substituted benzyl, silyl, C$_{1-6}$-alkoxymethyl, benzyloxymethyl, C$_{1-6}$-alkylsulphonyl, arylsulphonyl or acyl group;
R$^2$ and R$^3$ taken together form a cyclic acetal or ketal group;
R$^4$ is a hydrogen atom, methyl, C$_{1-6}$-alkoxyl, C$_{1-6}$-alkoxymethyl, allyl benzyloxymethyl, benzyloxyl, siloxyl or acyloxyl group;
comprising reacting an acetylene compound 10

with a nitrone defined by the general formula 11,

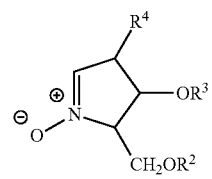

in the presence of a copper salt, a base and optionally a solvent.

2. The method according to claim 1, wherein the copper salt is a copper (I) salt, selected from the group consisting of copper(I) iodide, copper(I) bromide, copper(I) chloride, copper(I) acetate and copper(I) triflane.

3. The method according to claim 1, further comprising addition of a reducing compound to the copper salt, wherein the copper salt is selected from the group consisting of copper (II) sulphate, copper(II) chloride, and copper(II) acetate, and wherein the reducing compound is sodium ascorbate.

4. The method according to claim 1, wherein the ratio of copper salt to compound 10 is 3:1 or 0.01-1:1.

5. The method according to claim 1, wherein said base is a secondary or tertiary amine.

6. The method according to claim 5, wherein the amine is selected from the group consisting of a trialkylamine, an alkyldi(cycloalkyl)amines, dialkylamine possessing a branched alkyl substituent, a di(cycloalkyl)amine, and a heterocyclic amine.

7. The method according to claim 1, wherein the base is a trialkylamine, used in an amount of at least 3 equivalents relative to copper source.

8. The method according to claim 1, wherein the base is an alkali metal or an alkaline earth carbonate.

9. The method according to claim 1, wherein the base is a carbonate base selected from the group consisting of potassium carbonate, sodium carbonate, sodium bicarbonate and potassium bicarbonate.

10. The method according to claim 1, wherein the solvent is selected from the group consisting of aromatic hydrocarbons, chlorinated aliphatic hydrocarbons, aliphatic ethers, aliphatic nitiriles, and aliphatic N,N-di-(C$_{1-6}$ alkyl)amides.

11. The method according to claim 1, wherein the solvent is selected from the group consisting of acetonitrile, toluene, benzene, N,N-dimethylformamide, N,N-dimethylacetamide, tetramethylguanidine, HMPA, and N-methyl-pyrrolidone.

12. The method according to claim 1, wherein an acetylene compound defined by the general formula 10 is used as a starting material,

10 where:

$R^1$ is a $C_{1-6}$-alkyl, $C_{3-6}$-alkene, $C_{1-6}$-alkoxymethyl, benzyloxymethyl, hydroxy-$C_{1-6}$-alkyl, O-protected hydroxy-$C_{1-6}$-alkyl, dihydroxy-$C_{1-6}$-alkyl, and O,O'-protected dihydroxy-$C_{1-6}$-alkyl group.

13. The method according to claim 1, wherein the nitrone defined by the general formula 11 is used as a starting material,

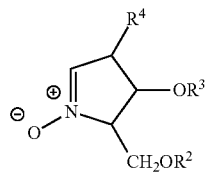

11 where:

$R^2$ is a $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl or acyl group;

$R^3$ is a $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl or acyl group;

$R^2$ and $R^3$ taken together form a cyclic acetal or ketal group;

$R^4$ is a hydrogen atom, or methyl, $C_{1-6}$-alkoxyl, $C_{1-6}$-alkoxymethyl, allyl, benzyloxymethyl, benzyloxyl, siloxyl or acyloxyl group.

14. The method according to claim 6, and a alkyldi(cycloalkyl)amine selected from the group consisting of triethylamine, N,N-diisopropylethylamine, wherein the alkyldi(cycloalkyl)amine is.

15. The method according to claim 6, wherein alkyldi(cycloalkyl)amines is selected from the group consisting of N-methyldicyclohexylamine, and tetramethylguanidine.

16. The method according to claim 6, wherein the dialkylamines possessing a branched alkyl substituent is diisopropylamine, dicyclohexylamine, or pyridine.

17. The method according to claim 12, wherein $R^1$ is selected from the group consisting of:

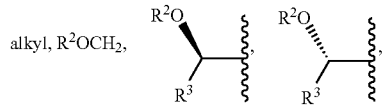

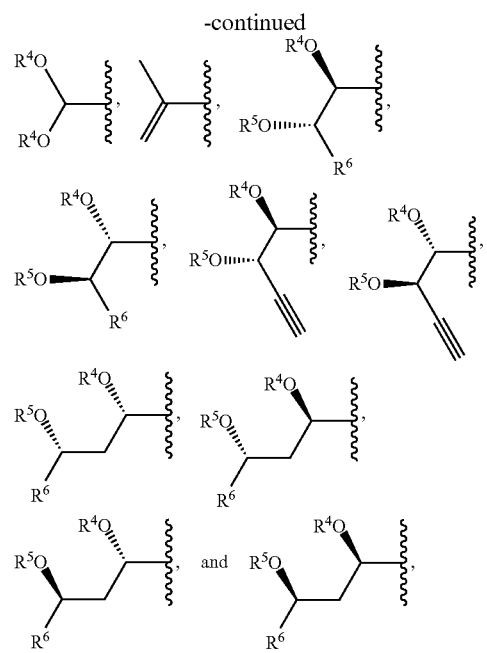

where:

$R^2$ is a $C_{1-6}$-alkyl, allyl, benzyl, $C_{1-6}$-alkoxymethyl, benzyloxymethyl, silyl, or acyl group;

$R^3$ is a $C_{1-6}$-alkyl or aryl group;

$R^4$ is a $C_{1-6}$-alkyl, allyl, benzyl, $C_{1-6}$-alkoxymethyl, benzyloxymethyl, silyl, or acyl group;

$R^5$ is a $C_{1-6}$-alkyl, allyl, benzyl, $C_{1-6}$-alkoxymethyl, benzyloxymethyl, silyl, or acyl group;

$R^4$ and $R^5$ taken together form a cyclic acetal or ketal group, or carbonate forming a fragment of the 1,3-dioxolane, 1,3-dioxane, or 1,4-dioxane ring;

$R^6$ is a hydrogen atom, linear or branched $C_{1-6}$-alkyl or aryl group.

18. A β-lactam compound of formula 9

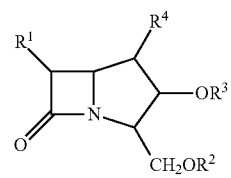

9 wherein $R^1$ is a compound selected from the group consisting of: a $C_{1-6}$ alkyl, $C_{3-6}$-alkene, $C_{1-6}$-alkoxymethyl, benzyloxymethyl, a hydroxy-$C_{1-6}$-alkyl, an O-protected hydroxy-$C_{1-6}$-alkyl, a dihydroxy-$C_{1-6}$-alkyl or an O,O'-protected dihydroxy-$C_{1-6}$ alkyl;

$R^2$ is a C-alkyl, allyl, benzyl, substituted benzyl, silyl, $C_{1-6}$-alkoxymethyl, benzyloxymethyl, $C_{1-6}$-alkylsulphonyl, arylsulphonyl and acyl group;

$R^3$ is a substituent selected from the group consisting of an $C_{1-6}$-alkyl, allyl, benzyl, substituted benzyl, silyl, $C_{1-6}$-alkoxymethyl, benzyloxymethyl, $C_{1-6}$-alkylsulphonyl, arylsulphonyl and acyl group;